(12) United States Patent
Kleinsek

(10) Patent No.: US 7,767,452 B2
(45) Date of Patent: Aug. 3, 2010

(54) TISSUE TREATMENTS WITH ADIPOCYTE CELLS

(76) Inventor: Don A. Kleinsek, W5036N County Highway A, Elkhart Lake, WI (US) 53020

(*) Notice: Subject to any disclaimer, the term of this patent is extended or adjusted under 35 U.S.C. 154(b) by 233 days.

(21) Appl. No.: 11/711,921

(22) Filed: Feb. 28, 2007

(65) Prior Publication Data

US 2007/0154461 A1   Jul. 5, 2007

Related U.S. Application Data

(63) Continuation of application No. 09/632,581, filed on Aug. 3, 2000, now abandoned, which is a continuation of application No. 09/003,378, filed on Jan. 6, 1998, now abandoned.

(60) Provisional application No. 60/037,961, filed on Feb. 20, 1997.

(51) Int. Cl.
*C12N 5/071* (2010.01)
*A61K 35/12* (2006.01)

(52) U.S. Cl. ..................... 435/366; 424/93.7
(58) Field of Classification Search ............ None
See application file for complete search history.

(56) References Cited

U.S. PATENT DOCUMENTS

| | | | |
|---|---|---|---|
| 3,600,718 A | 8/1971 | Boone | |
| 3,665,520 A | 5/1972 | Perras et al. | |
| 3,911,503 A | 10/1975 | Hankin | |
| 3,949,073 A * | 4/1976 | Daniels et al. ............. | 514/2 |
| 4,100,627 A | 7/1978 | Brill, III | |
| 4,139,619 A | 2/1979 | Chidsey, III | |
| 4,172,298 A | 10/1979 | Rechenberg | |
| 4,234,599 A | 11/1980 | Van Scott et al. | |
| 4,298,998 A | 11/1981 | Naficy | |
| 4,377,584 A | 3/1983 | Rasmusson et al. | |
| 4,401,308 A | 8/1983 | Sakaguchi et al. | |
| 4,424,208 A | 1/1984 | Wallace et al. | |
| 4,488,911 A | 12/1984 | Luck et al. | |
| 4,551,270 A | 11/1985 | Danos et al. | |
| 4,582,640 A | 4/1986 | Smestad et al. | |
| 4,612,331 A | 9/1986 | Barratt et al. | |
| 4,642,117 A | 2/1987 | Nguyen et al. | |
| 4,684,522 A | 8/1987 | Marissal et al. | |
| 4,760,071 A | 7/1988 | Rasmusson et al. | |
| 4,772,284 A | 9/1988 | Jefferies et al. | |
| 4,790,848 A | 12/1988 | Cronin | |
| 4,803,075 A | 2/1989 | Wallace et al. | |
| 4,837,379 A | 6/1989 | Weinberg | |
| 4,840,628 A | 6/1989 | Cavon | |
| 4,882,166 A | 11/1989 | Graham et al. | |
| 4,919,664 A * | 4/1990 | Oliver et al. ............. | 128/898 |
| 4,969,912 A | 11/1990 | Kelman et al. | |
| 5,002,071 A | 3/1991 | Harrell | |
| 5,030,451 A | 7/1991 | Trebosc et al. | |
| 5,037,803 A | 8/1991 | Gueyne et al. | |
| 5,116,605 A | 5/1992 | Alt | |
| 5,140,200 A | 8/1992 | Stanton | |
| 5,192,312 A | 3/1993 | Orton | |
| 5,194,259 A | 3/1993 | Soudant et al. | |
| 5,197,983 A | 3/1993 | Berman et al. | |
| 5,199,942 A * | 4/1993 | Gillis ......................... | 604/4.01 |
| 5,215,759 A | 6/1993 | Mausner | |
| 5,332,802 A | 7/1994 | Kelman et al. | |
| 5,366,498 A | 11/1994 | Brannan et al. | |
| 5,376,117 A | 12/1994 | Pinchulk et al. | |
| 5,422,261 A | 6/1995 | Lee et al. | |
| 5,449,757 A * | 9/1995 | Serrero ...................... | 530/350 |
| 5,480,644 A | 1/1996 | Freed | |
| 5,510,102 A | 4/1996 | Cochrum | |
| 5,516,532 A | 5/1996 | Atala et al. | |
| 5,516,779 A | 5/1996 | Von Langen et al. | |
| 5,523,090 A | 6/1996 | Znaiden et al. | |
| H1610 H | 11/1996 | Luo et al. | |
| 5,587,396 A | 12/1996 | Smith | |
| 5,591,444 A | 1/1997 | Boss, Jr. | |
| 5,599,788 A | 2/1997 | Purchio et al. | |
| 5,656,478 A | 8/1997 | Tanagho et al. | |

(Continued)

FOREIGN PATENT DOCUMENTS

EP    0 106 501 B1    1/1988

(Continued)

OTHER PUBLICATIONS

Gruber, et al., Laryngo-Rhino-Otol., 1996, vol. 75, pp. 105-108.*

(Continued)

*Primary Examiner*—Jon P Weber
*Assistant Examiner*—L J Schuberg

(57) ABSTRACT

Certain embodiments here in are directed to a method of treating a tissue associated with a defect in a human including wrinkles, rhytids, depressed scar, cutaneous depressions, stretch marks, hyperplasia of the lip, nasolabial fold, melolabial fold, scarring from acne vulgaris, and post-rhinoplasty irregularity. The tissue defect may be treated by introducing a plurality of in vitro cultured autologous fibroblast cells at or proximal to the defect area of the patient's tissue. The autologous fibroblast cells may have been cultured in vitro to expand the number of fibroblast cells in at least one medium that comprises autologous serum. The autologous fibroblast cell cultures may be derived from connective tissue, dermal, fascial fibroblasts, papillary fibroblasts, and/or reticular fibroblasts.

27 Claims, No Drawings

U.S. PATENT DOCUMENTS

| | | | |
|---|---|---|---|
| 5,667,778 | A | 9/1997 | Atala |
| 5,709,854 | A | 1/1998 | Griffith-Cima et al. |
| 5,759,190 | A | 6/1998 | Vibe-Hansen et al. |
| 5,763,399 | A | 6/1998 | Lee |
| 5,830,708 | A | 11/1998 | Naughton |
| 5,842,477 | A * | 12/1998 | Naughton et al. ............ 128/898 |
| 5,858,390 | A | 1/1999 | Boss, Jr. |
| 5,863,531 | A * | 1/1999 | Naughton et al. .......... 424/93.7 |
| 5,888,551 | A | 3/1999 | Jimenez et al. |
| 6,044,846 | A | 4/2000 | Edwards |
| 6,060,053 | A | 5/2000 | Atala |
| 6,092,528 | A | 7/2000 | Edwards |
| 6,156,032 | A | 12/2000 | Lennox |
| 6,325,798 | B1 | 12/2001 | Edwards et al. |
| 6,355,239 | B1 | 3/2002 | Bruder et al. |
| 6,432,710 | B1 | 8/2002 | Boss, Jr. et al. |
| 6,497,875 | B1 | 12/2002 | Sorrell et al. |
| 6,802,841 | B2 | 10/2004 | Utley et al. |
| 6,866,842 | B1 | 3/2005 | Chancellor et al. |
| 6,878,383 | B2 | 4/2005 | Boss et al. |
| 7,115,274 | B2 | 10/2006 | Keller et al. |
| 2002/0055786 | A1 | 5/2002 | Atala |

FOREIGN PATENT DOCUMENTS

| | | |
|---|---|---|
| EP | 0 260 787 A1 | 3/1988 |
| EP | 0282 746 | 9/1988 |
| EP | 0 416 846 A3 | 1/1992 |
| EP | 0 717 983 | 1/2001 |
| EP | 0 728 472 | 6/2004 |
| EP | 0 728 471 | 11/2004 |
| FR | 2499405 | 4/1983 |
| FR | 2554344 | 9/1986 |
| JP | 01-256967 | 10/1989 |
| WO | WO 95/25549 | 9/1995 |
| WO | WO 96/31192 | 10/1996 |
| WO | WO 97/04720 | 2/1997 |
| WO | WO 97/14412 | 4/1997 |
| WO | WO 97/18842 A1 | 5/1997 |
| WO | WO 97/36570 | 10/1997 |
| WO | WO 98/33889 A1 | 8/1998 |
| WO | WO 98/36704 | 8/1998 |
| WO | WO 98/36705 | 8/1998 |
| WO | WO 98/40027 | 9/1998 |
| WO | WO 99/07416 | 2/1999 |
| WO | WO 99/43270 | 9/1999 |
| WO | WO 99/47112 | 9/1999 |
| WO | WO 00/73418 | 12/2000 |

OTHER PUBLICATIONS

Billings, et al., Plastic and Reconstructive Surgery, Feb. 1989, vol. 83, No. 2, pp. 368-381.*

Smith,V., Anatomical Record, 1971, vol. 169, pp. 97-104.*

Green et al., "Formation of Normally Differentiated Subcutaneous Fat Pads by an Established Preadipose Cell Line", Journal of Cell. Physiol. 1979, vol. 101, pp. 169-171 (no p. 172 found in databases).*

Nakajima et al. "Adipose tissue extracellular matrix: newly organized by adipocytes during differentiation" Differentiation 1998, vol. 63, pp. 193-200.*

Shigeno et al. "Human Bone-Cell Proliferation in Vitro Decreases With Human Donor Age" The Journal of Bone and Joint Surgery, 1995, vol. 77-B, No. 1, pp. 139-142.*

Van et al., Cell Tissue Res 225: 557-566 (1982).*

Oral Disclosure of Kawaguchi et al. at the Annual Meeting of the Japanese Association for Animal Cell Technology, Nov. 6-10, 1995—see Proceedings, pp. 501-504 (published 1997).*

Hazen et al., Journal of Lipid Research 36:868-875 (1995).*

Hausman et al., J. Anim. Sci. 74 : 2117-2128 (1996).*

Christian Dani, Embryonic Stem Cell-Derived Adipogenesis, 165 Cells Tissues Organs 173-180 (1999).*

Douglas et al., "Visualization of Cellular Aggregates cultured on a three Dimensional Collagen Sponge Matrix", In Vitro 16(4):306-12; 1980.

Duarte C. et al., "Gingival Connective Tissue Allograft between Identical Twins: A Case Report", *J. Esthet. Dent.*; 8(6):269-227 (1996).

Durselen et al., "Comparative Animal Study of Three Ligament Prostheses for the rReplacement of the Anterior Cruciate and Medial Collateral Ligament", *Biomaterial*, 17(10):977-982 (1996).

Ersck, "Transplantation of Purified Autologous Fat: A 3-Year Follow-Up is Disappointing", *Plastic & Reconstructive Surgery*, 87(2):21926; 1991.

Folkman et al., "Angiogenesis in vitro" *Nature*, 288:55156; 1980.

Francey et al., "Culture of Ovine Bone Marrow-Derived Macrophages and Evidence for Serum Factors Distinct from M-CSF Contributing to Their Propagation in Vitro", *J. of Leukocyte Bio.*, 51:525-34; 1992.

Frey et al., "Endoscopic Subureteral Collagen Injection for the Treatment of Vesicoureteral Reflux in Infants and Children", *J. Urol.*; 154:804-807 (1994).

Gabriel et al., "Risk of Connective-tissue Diseases and other Disorders after Breast Implantation", *N. Engl. J. Med.*; 330(24):1697-1702 (1994).

Gruber et al. "In Vitro Cultivation of Human Chondrocytes Using Autologous Human Serum Suppoemented Culture Medium: Minimizing Possible risk of Infection with Pathogens of Prion Diseases", *Laryngorhinootologle*, 75(2):105-108 (1996)-Abstract.

Gold, "The Fibrel Mechanism of Action Study—A Preliminary Report", *J. Dermatologic Surg. Oncology*, 20:586-90; 1994.

Kaufman, "Androgen Metabolism as it Affects Hair Growth in Androgenetic Alopecia", *Derm. Clin.*, 14:4, 697-711 (1996).

Kilner et al., "Skin-Grafting in the Buccal Cavity", *Br. J. Surg.*; 9:148-154 (1921).

Kessler et al., "A Call for Higher Standards for Breast Implants", *JAMA*, 270(21):2607-2608 (1993).

Koller et al., "Alternatives to Animal Sera for Human Bone Marrow Cell Expansion: Human Serum and Serum-Free Media", *J. of Hematotherapy*, 7: 413-23; 1998.

Korotzer et al., "Complement-Dependent Induction of DNA Synthesis and Proliferation of Human Diploid Fibroblasts", *Journal of Cellular Physiology*, 105:503-512 (1980).

Leighton et al., "A Sponge Matrix Method for Tissue Culture. Formation of Organized Aggregates of Cells in Vitro", *J. Nat'l Cancer Ins*, 545-61; 1951.

Leighton et al., "Patterns of Three-dimensional Growth in Vitro in Collagen-coated Cellulose Sponge: Carcinomas and Embryonic Tissues", *Cancer Res.* 28:286-96, 1968.

Leonard et al. "Endocopic Injection of Glutaraldehyde Cross-linked Bovine Dermal Collagen for Correction of Vesicoureteral Reflux", *J. Urol.*, 145:115-119 (1991).

Lewis, "The Current Status of Autologous Fat Grafting", *Aesth. Plas. Surg.*, 17:109-112 (1993).

Lin et al., "Ligament Tissue Engineering using Synthetic Biodegradable Fiber Scaffolds", *Tiss. Engin.*,5(5):443-452 (1999).

Millikan et al., "5-year Safety and Efficacy Evaluation with Fibrel in the Correction of Putaneous Scars Following One or Two Treatments", *J. Dermatol. Surg. Oncol*, 17:223-29; 1991.

Monga et al., "Periurethral Collagen Injections for Genuine Stress Incontinence: a 2-Year Follow-up", *British Journal of Urology*, 76:156-160 (1995).

O'Donague et al., "Repair of the Anterior Curciate Ligament in Dogs", *J. Bone Joint Surge.*, 48-A(3):503-519 (1996).

O'Donnell et al., "Technical Refinements in Endoscopic Correction of Vesicoureteral Reflux", *J. Urol.*; 140:1101-1102 (1988).

On-Line Medical Dictionary 1997, http://cancerweb.ncl.ac.uk/cgi-bin/omd?growth+medium, p. 1.

Oppenlander et al., "Serum-Fee Expansion of CD34NEG Cord Blood Cells in Enhanced by Low Levels of Fetal Bovine Serum but not Autologous Serum", 44th Annual Meeting of the American Society of Hematology, Dec. 6-20, 2002 (Abstract).

Oral Disclosure of Kawaguchi et al. at the Annual Meeting of the Japanese Association for Animal Cell Technology, Nov. 6-10, 1995- see Proceedings, pp. 501-504 (published 1997).

Ozgentas et LA., "A Comparison of Soft-Tissue Substitutes" *Ann. Plastic Surgery* 33(2):171-77; 1994.

Percoraro et al., "Cycle of the Scalp Hiar of the New-Born Child", *J. Invest. Dermatol.*; 43:145-146 (1964).

Peters, "Failure Properties of Leaf Valve Inflatable Saline Breast Implants", *Can. J. Pastic Surg.*, 5(4):241-245 (1997).

Hasholt, "Behavior of Cell Cultures from Human Amniotic Fluid", *Journal of Medical Genetics*, 13:34-37 (1976).

ten Kate, et al., "Serum Dependence of Cellular Phenotype in Mucopolysaccaridoses: The Influcence of Autologous Serum on Metachromasia" *Humangenetik*, 18:95-98 (1973).

Adachi et al., "The Metabolism and Control Mechanism of Human Hair Follicles", *Curr. Probl. Dermatol.*; 5:37-78 (1973).

Agren et al., "Collagenase in Wound Healing: Efect of Wound Age and Type", *J. Invest. Dermatol.*, 99:709-714 (1992).

Ahmad et al., "Alopecia Universalis Associated with a Mutation in the Human *hairless* Gene", *Science*; 279:720-724 (1998).

Allografts in Orthopaedic Practice, Czitrom et al., (eds.) William & Wilkins, Baltimore (1992), pp. 1-10.

Angell et al., "After Quinlan: The Dilemma of the Persistent Vegetative State", *N. Engl. J. Med.*330(24):1524-1525 (1994).

Arnoczsky et al, "Anterior Cruciate Ligament Replacement Using Patellar Tendon: An Evaluation of Graft Revascularization in the Dog", *Journal of Bone and Joint Surgery*, 64-A(2):217-224, Feb. 1982.

Atlas of Cosmetic & Reconstructive Periodontal Surgery, Cohen (ed)., Lea & Febinger, Philadelphia (1988).

Bailey and Love's Short Practice of Surgery, $22^{nd}$ Ed., Mann et al. (eds.), Chapman and Hall Medical, London (1995).

Bell et al., "The Reconstitution of Living Skin", *J. Investigative Dermatology* 81:(1) 2s-10s; 1983.

Billings et al., "Historical Review and Present Status of Free Fat Graft Autotransplantation in Plastic and Reconstructive Surgery", *Plast Reconsstr Surg.*, 83(2): 368-381, Feb. 1989.

Bondurant et al., Safety of Silicone Impants, Institute of Medicine Nat'l Acad. Press, Washington, D.C., Executive Summary (1999).

Border et al., "Transforming Growth Factor β in Tissue Fibrosis", *N. Engl. J. Med.*; 331:1286-1292 (1994).

Brittberg, "Treatment of Deep Cartilage Defects in the Knee with Autologous Chondrocyte Transplantation", *The New England Journal of Medicine*, 331(14):889-895; 1994.

Callan et al., "Use of Bovine-Derived Hydroxyapatite in the Treatment of Edentulous Ridge Defects: A Human Clinical and Histologic Case Report", J. Peridontol., 64:575-582 (1993).

Campbell's Operative Orthopaedics, $9^{th}$ Ed., Canale (ed.), Mosby, St. Louis (1998), pp. 1-42.

Campbell's Urology, $7^{th}$ Ed., Walsh et al.(eds.), Saunders, Philadelphia (1997), pp. 1-37.

Chen et al., "Materials Design Analysis of the Prosthetic Anterior Cruciate Ligament", *J. Biomed. Mater. Res*, 14:567-585 (1990).

Choi et al., "The Effect of Serum on Monolayer Cell Culture of Mammalian Articular Chondrocytes", *Connective Tissue Research* (7) 105-12: 1980.

Conrad et al., "Relative Distribution of Actin, Myosin I and Myosin II during the Wound Healing Response of Fibroblasts", *J. Cell Biolo.*; 120(6):1381-1391 (1993).

Davis et al., "Autologous Free Dermal Fat Graft," *Arch. Of Otolaryngology—Head and Neck Surgery* 121:95-100; 1985.

Delustro et al., "Raction to Injectable Collagen" Results in Animal Models and Clinical Use, *Plastic and Reconstructive Surgery* 79:581-99; 1987.

Desmouliere, "Factors Influencing Myofibroblast Differentiation during Wound Healing and Fibrosis", *Cell Biol. Int.*, 19(5):471-476 (1995).

Hamilton, "Male Hormone Stimulation is Prerequisite and an Incitant in Common Baldness", *Am. J. Anat.*; 71:451-481 (1942).

Hansborough et al., "Burn Wound Closure with Cultured Autologous Keratinocytes and Fibroblasts Attached to a Collagen-Glycosaminoglycan Substrate", *JAMA*, 136:2125-30; 1989.

Harrison's Principles of Internal Medicine $15^{th}$ Ed., Braunwald et al. (eds.) McGraw-Hill, NY (2001), pp. 1-27.

Hausman et al., "The Influence of Extracellular Matrix Substrata on Preadipocyte Development in Serum-Free Cultures of Stromal-Vascular Cells", *J. Anim. Sci.* 74(9):2117-2128 (1996).

Hausman et al. "Adipocyte Devolopment in the Rat Hypodermis", The *American Journal of Anatomy*, 161:85-100 (1981).

Hazen et al., "Monolayer Cell Culture of Freshly Isolated Adipocytes Using Extracellular Basement Membrane Components", *J. Lupid Res.*, 36(4):868-875 (1995).

Health, "Study: Stem cell lines contaminated", www.cnn.com, Jan. 23, 2005, pp. 1-3.

Henley et al., "Particulate Silicone for Use in Periurethral Injections: Local Tissue Effects and Search for Migration", *J. Urol.*; 153:2039-2043 (1995).

Kageyama et al., "Collagen Implantation for Post-Prostatectomy Incontinence: Early Experience with a Transrectal Ultrasonographically Guided Method", J. Urol.; 152:1473-1475 (1994).

Kaplan et al., "The Endoscopic Correction of Reflux by Polytetrafluoroethylene Injection", *J. Urol.*; 138:953-955 (1987).

Ludwig, "Classification of the Types of Androgenetic Alopecia (common baldness) Occurring in the Female Sex" *Br. J. Dermatol.*; 97(3):247-254 (1977).

Malizia et al., Migration and Granulomatous Reaction after Periurethral Injection of Polytef (Teflon) *JAMA*, 251(24):3277-81; 1984.

Matton et al., "The Histroy of Injectable Biomaterials and the Biology of Collagen" *Aesthetic Plastic Surgery*, 9:133-40; 1985.

Matthews et al., "Persistence of Autologous Free Fat Transplant in Bladder Submucosa of Rats", *J. Urol.*; 152:819-821 (1994).

Matti et al., "Clinical Use of Zyplast in Correction of Age- and Disease-Related Contour Deficiencies of the Face", *Aesth. Plast. Surg.*, 14:227-234 (1990).

Maves et al., "Phonosurgery: Indications and Pitfalls" *Ann. Otol. Rhinol. Laryngol.*, 98:577-80; 1989.

Mcguire et al., "Transurethral Collagen Injection for Urinar Incontinence", *Urol.*; 43(4):413-415 (1994).

McKinney et al., "Use of Pubic Fat as a Graft for Eyelid Defects", *Aesth. Plast. Surg.*, 18:383-385 (1994).

Menetrey et al., "Direct-, Fibroblast- and Myoblast-Mediated Gene Transfer to the anterior Cruciate Ligament", *Tiss. Engin.*; 5(5):435-442 (1999).

Mercer's Orthopedic Surgery, $9^{th}$ Ed., Duthie et al. (eds.), Arnold London (1996), pp. 1-8.

Millikan et al., "Treatment of Depressed Cutaneous Scars with Gelatin Matrix Implant: A Multicenter Study" *J. of the Amer. Acad. of Dermatol.*, 16(6):1155-162; 1987.

Politano et al., "Periurethral Teflon Injection for Urinary Incontinence", *J. Urol.*; 111:180-183 (1985).

Principles of Surgery, $7^{th}$ Ed., Schwartz et al. (eds.), McGraw-Hill, NY (1999), pp. 1-11.

Rougraff et al., "Arthroscopic and Histologic Analysis of Human Patellar Tendon Autografts Used for Anterior Cruciate Ligament Reconstruction", *Am. J. Sports Med.*, 21(2):277-284 (1993).

Rowden et al., "Antigens Specified by the Tla Locus Are Expressed on the Surface of Murine Langerhans Cells" The Journal of Investigative Dermatology, 81:2-6 (1983).

Santarosa et al., "Periurethral Injection of Autologous Fat for the Treatement of Sphincteric Incontinence", *J. Urol.*,151:607-611 (1994).

Schaffer et al., "Lymphocyte Function in Wound Healing and Following Injury", *Br. J. Surg*, 85:444-460 (1998).

Schwartz et al., "Serum From Outdated Human Platelet Concentrates: An Alternative Supplement for Tissue (Fibroblast) Culture Media", American Journal of Hematology, 17:23-27 (1984).

Shearburn et al., "Shouldice Repair for Inguinal Hernia", *Surg.*; 66(2):450-459 (1969).

Sirica et al., "Use of Primary Cultures of Adult Rat Hepatocytes on Collagen Gel-Nylong Mesh to Evaluate Carcinogen-Induced Unscheduled DNA Synthesis", *Cancer Res.* 40:3259-65; 1980.

Slanetz et al., "The Intra-Oral Use of Split-Thickness Skin Grafts in Head and Neck Surgery", *Am. J. Surg.*, 104:721-726 (1962).

Smith's Textbook of Endorology, Smith et al. (eds.) QMP, St. Louis, Missouri (1996), pp. 1-14.

Sogin et al., "Long Lived Nonadherent Rabbit macrophages Obtained from Spleen Cell Cultures", in Vitro, 19(2):90-98; 1983.

Sorour et al., "Infiltrative Potentiality of Brain Tumors in Organ Culture" *J Neurosurg.* 43:742-49; 1975.

Spira et al., "Injectable Soft tissue Substitutes", *Clin. Plastic Surgery* 20(1):181-88; 1993.

Sporn et al., "Mini-Review: Some Recent Advances in the Chemistry and Biology of Transforming Growth Factor-Beta", *J. Cell Biol.*; 105:1039-1045 (1987).

Stenberg et al., "A New Bioimplant for the Endoscopic Treatment of Vesicoureteral Reflux: Experimental and Short-term Clinical Results", *J. Urol*, 154:800-803 (1995).

Surgery: Scientific Principles and Practice, Chap. 3, Cohen et al., Philadelphia, PA, JB Lippincott (1993), pp. 1-22, pp. 86-102.

Textbook of Dermatology; 2:1937, Rook (eds.) Blackwell, Oxford (1986), pp. 5-39.

Travis, "Hormone Helps Ring Internal Alarm Clock", *Sci. News*, 155(2):396 (1999).

Tsai et al., "Clinical Results of Cultured Epithelial Cell Grafting in the Oral and Maxillofacial Region", *J. Craniomaxillofac. Sur.*, 25:4-8 (1997).

Ueda et al., "Peri-implant Soft Tissue management Through Use of Cultured Mocosal Epithelium", *Oral Surg. Oral Med. Oral Pathol. Oral Radiol. Endod.*; 86:393-400 (1998).

Usher, "The Repair of Incisional and Inguinal Hernias", *Surg. Gynecol. Obstet.*; 131:525-530 (1970).

Van et al. "Complete Differentiation in Vivo of Implanted Cultured Adipocyte Precursors from Adult Rats" *Cell Tissue Res.* 225(3):557-566 (1982).

Walker et al., "Injectable Bioglass as a Potential Substitute for Injectable Polytetrafluoroethylene", *J. Urol.*, 148:645-647 (1992).

Wound Healing: Biochemical and Clinical Aspects, Cohen et al., (eds.) Philadelphia, WB Saunders (1992), pp. 1-25.

Yang et al., "Sustaned Growth in Primary Culture of Normal Mammary Epithelial Cells Embedded in Collagen Gels", *Proc. Nat'l. Acad. Sci.*, 77(4):2088-92, 1980.

Yang et al., "Effects of Hormones and Growth Factors on Human Mammary Epithelial Cells in Collagen Gel Culture", *Can. Res.* 41:1021-27; 1981.

Zhao et al, "Serum-free culture of Dendritic Cells from Patients with Chronic Myeloid Leukemia in Vitro and Estimation of Their Cytotoxicity", *Chin Med. J.* 115:1296-1300 (2002)(Abstract).

U.S. Appl. No. 09/632,581 entitled "Augmentation and Repair of Tissue Defects" filed Aug. 3, 2000 by Donald A. Kleinsek, pp. 1-54.

U.S. Appl. No. 10/129,180 entitled "Augmentation and Repair of Age-Related Soft Tissue Defects" filed May 3, 2002 by Donald A. Kleinsek, pp. 1-99.

\* cited by examiner

TISSUE TREATMENTS WITH ADIPOCYTE CELLS

REFERENCE TO RELATED APPLICATIONS

This application is a continuation of U.S. patent application Ser. No. 09/632,581, filed Aug. 3, 2000 now abandoned, which is a continuation of abandoned U.S. patent application Ser. No. 09/003,378, filed on Jan. 6, 1998, which claims priority to U.S. Patent Application No. 60/037,961, filed on Feb. 20, 1997, which patent applications are hereby incorporated by reference herein.

FIELD OF INVENTION

The field of the present invention is the long-term augmentation and/or repair of dermal, subcutaneous, or vocal cord tissue.

BACKGROUND OF INVENTION

I. In Vitro Cell Culture

The majority of in vitro vertebrate cell cultures are grown as monolayers on an artificial substrate which is continuously bathed in a nutrient medium. The nature of the substrate on which the monolayers may be grown may be either a solid (e.g., plastic) or a semi-solid (e.g., collagen or agar). Currently, disposable plastics have become a preferred substrate for cell culture.

While the growth of cells in two-dimensions is frequently used for the preparation and examination of cultured cells in vitro, it lacks the characteristics of intact, in vivo tissue which, for example, includes cell-cell and cell-matrix interactions. Therefore, in order to characterize these functional and morphological interactions, various investigators have examined the use of three-dimensional substrates in such forms as a collagen gel (Yang et al., Cancer Res. 41:1027 (1981); Douglas et al., In Vitro 16:306 (1980); Yang et al., Proc. Nat'l Acad. Sci. 2088 (1980)), cellulose sponge (Leighton et al., J. Nat'l Cancer Inst. 12:545 (1951)), collagen-coated cellulose sponge (Leighton et al., Cancer Res. 28:286 (1968)), and GELFOAM® (Sorour et al., J. Neurosurg. 43:742 (1975)). Typically, these aforementioned three-dimensional substrates are inoculated with the cells to be cultured, which subsequently penetrate the substrate and establish a "tissue-like" histology similar to that found in vivo. Several attempts to regenerate "tissue-like" histology from dispersed monolayers of cells utilizing three-dimensional substrates have been reported. For example, three-dimensional collagen substrates have been utilized to culture a variety of cells including breast epithelium (Yang, Cancer Res. 41:1021 (1981)), vascular epithelium (Folkman et al., Nature 288:551(1980)), and hepatocytes (Sirica et al., Cancer Res. 76:3259 (1980)), however long-term culture and proliferation of cells in such systems has not yet been achieved. Prior to the present invention, a three-dimensional substrate had not been utilized in the autologous in vitro culture of cells or tissues derived from the dermis, fascia, or lamina propria.

II. Augmentation and/or Repair of Dermal and Subcutaneous Tissues

In the practice of cosmetic and reconstructive plastic surgery it is frequently necessary to employ the use of various injectable materials to augment and/or repair defects of the subcutaneous or dermal tissue, thus effecting an aesthetic result. Non-biological injectable materials (e.g., paraffin) were first utilized to correct facial contour defects as early as the late nineteenth century. However, numerous complications and the generally unsatisfactory nature of long-term aesthetic results caused the procedure to be rapidly abandoned. More recently, the use of injectable silicone became prevalent in the 1960's for the correction of minor defects, although various inherent complications also limited the use of this substance. Complications associated with the utilization of injectable liquid silicone include local and systemic inflammatory reactions, formation of scar tissue around the silicone droplets, rampant and frequently-distant unpredictable migration throughout the body, and localized tissue breakdown. Due to these potential complications, silicone is not currently approved for general clinical use. Although the original proponents of silicone injection have continued experimental programs utilizing specially manufactured Medical Grade silicone (e.g., Dow Corning MDX 4.4011®) with a limited number of subjects, it appears highly unlikely that its use will be generally adopted by the surgical community. See e.g., Spira and Rosen, Clin. Plastic Surgery 20:181 (1993); Matton et al., Aesthetic Plastic Surgery 9:133 (1985).

It has also been suggested to compound extremely small particulate species in a lubricious material and inject such combination micro-particulate media subcutaneously for both soft and hard tissue augmentation and repair, however success has been heretofore limited. For example, bioreactive materials such as hydroxyapatite or cordal granules (osteo conductive) have been utilized for the repair of hard tissue defects. Subsequent undesirable micro-particulate media migration and serious granulomatous reactions frequently occur with the injection of this material. These undesirable effects are well-documented with the use of such materials as polytetrafluoroethylene (TEFLON®) spheres of small diameter (~90% of particles having a diameter of 30 µm) in glycerin. See e.g., Malizia et al., JAMA 251:3277 (1984). Additionally, the use of very small diameter particulate spheres (~1-20 µm) or small elongated fibrils (~1-30 µm in diameter) of various materials in a biocompatible fluid lubricant as injectable implant composition are disclosed in U.S. Pat. No. 4,803,075. However. while these aforementioned materials create immediate augmentation and/or repair of defects, they also have a tendency to migrate and be reabsorbed from the original injection site.

The poor results initially obtained with the use of non-biological injectable materials prompted the use of various non-immunogenic, proteinaceous materials (e.g., bovine collagen and fibrin matrices). Prior to human injection, however, the carboxyl- and amino-terminal peptides of bovine collagen must first be enzymatically-degraded, due to its highly immunogenic nature. Enzymatic degradation of bovine collagen yields a material (atelbcollagen) which can be used in limited quantities in patients pre-screened to exclude those who are immunoreactive to this substance. The methodologies involved in the preparation and clinical utilization of atelocollagen are disclosed in U.S. Pat. Nos. 3,949,073; 4,424, 208; and U.S. Pat. No. 4,488,911. Atelocollagen has been marketed as ZYDERM® brand atelocollagen solution in concentrations of 35 mg/ml and 65 mg/ml. Although atelocollagen has been widely employed, the use of ZYDERM® has been associated with the development of anti-bovine antibodies in approximately 90% of patients and with overt immunologic complications in 1-3% of patients. See DeLustro et al., Plastic and Reconstructive Surgery 79:581 (1987).

Injectable atelocollagen solution also was shown to be absorbed from the injection site, without replacement by host material, within a period of weeks to months. Clinical protocols calling for repeated injections of atelocollagen are, in practice, primarily limited by the development of immunogenic reactions to the bovine collagen. In order to mitigate these limitations, bovine atelocollagen was further processed by cross-linking with 0.25% glutaraldehyde, followed by filtration and mechanical shearing through fine mesh. The methodologies involved in the preparation and clinical utilization of this material are disclosed in U.S. Pat. Nos. 4,582,640 and 4,642,117. The modified atelocollagen was marketed as ZYPLAST® brand cross-linked bovine atelocollagen. The propertied advantages of cross-linking was to provide increased resistance to host degradation, however this was off-set by an increase in solution viscosity. In addition, cross-linking of the bovine atelocollagen was found to decrease the number of host cells which infiltrated the injected collagen site. The increased viscosity, and in particular irregular increased viscosity resulting in "lumpiness," not only rendered the material more difficult to utilize, but also made it unsuitable for use in certain circumstances. See e.g., U.S. Pat. No. 5,366,498. In addition, several investigators have reported that there is no or marginally-increased resistance to host degradation-of ZYPLAST® cross-linked bovine atelocollagen in comparison to that of the non-cross-linked ZYDERM® atelocollagen and that the overall longevity of the injected material is, at best, only 4-6 months. See e.g., Ozgentas et al., Ann. Plastic Surgery 33:171 (1994); and Matti and Nicolle, Aesthetic Plastic Surgery 14:227 (1990). Moreover, bovine atelocollagen cross-linked with glutaraldehyde may retain this agent as a high molecular weight polymer which is continuously hydrolyzed, thus facilitating the release of monomeric glutaraldehyde. The monomeric form of glutaraldehyde is detectable in body tissues for up to 6 weeks after the initial injection of the cross-linked atelocollagen. The cytotoxic effect of glutaraldehyde on in vitro fibroblast cultures is indicative of this substance not being an ideal cross-linking agent for a dermal equivalent which is eventually infiltrated by host cells and in which the bovine atelocollagen matrix is rapidly degraded, thus resulting in the release of monomeric glutaraldehyde 5 into the bodily tissues and fluids.

Similarly, chondroitin-6-sulfate (GAG), which weakly binds to collagen at neutral pH, has also been utilized to chemically modify bovine protein for tissue graft implantation. See Hansborough and Boyce, JAMA 136:2125 (1989). However, like glutaraldehyde, GAG may be released into the tissue causing unforeseen long-term effects on human subjects. GAG has been reported to increase scar tissue formation in wounds, which is to be avoided in grafts. Additionally, a reduction of collagen blood clotting capacity may also be deleterious in the application in bleeding wounds, as fibrin clot contributes to an adhesion of the graft to the surrounding tissue.

The limitations which are imposed by the immunogenicity of both modified and non-modified bovine atelocollagen have resulted in the isolation of human collagen from placenta (see e.g., U.S. Pat. No. 5,002,071) from surgical specimens (see e.g., U.S. Pat. Nos. 4,969,912 and 5,332,802); and cadaver (see e.g., U.S. Pat. No. 4,882,166). Moreover, processing of human-derived collagen by cross-linking and similar chemical modifications is also required, as human collagen is subject to analogous degradative processes as is bovine collagen. Human collagen for injection, derived from a sample of the patient's own tissue, is currently available and is marketed as AUTOLOGEN®. It should be noted, however, that there is no quantitative evidence which demonstrates that human collagen injection results in lower levels of implant degradation than that which is found with bovine collagen preparations. Furthermore, the utilization of autologous collagen preparation and injection is limited to those individuals who have previously undergone surgery, due to the fact that the initial culture from which the collagen is produced is derived is from the tissue removed during the surgical procedure. Therefore, it is evident that, although human collagen circumvents the potential for immunogenicity exhibited by bovine collagen, it fails to provide long-term therapeutic benefits and is limited to those patient who have undergone prior surgical procedures.

An additional injectable material currently in use as an alternative to atelocollagen augmentation of the subjacent dermis consists of a mixture of gelatin powder, -aminocapronic acid, and the patient's. plasma marketed as FIBREL®. See Multicenter Clinical Trial, J. Am. Acad. Dermatology 16:1155 (1987). The action of FIBREL® appears to be dependent upon the initial induction of a sclerogenic inflammatory response to the augmentation of the soft tissue via the subcutaneous injection of the material. See e.g., Gold, J. Dermatologic Surg. Oncology, 20:586 (1994). Clinical utilization of FIBREL® has been reported to often result in an overall lack of implant uniformity (i.e., "lumpiness") and longevity, as well as complaints of patient discomfort associated with its injection. See e.g., Millikan et al., J. Dermatologic. Surg. Oncology, 17:223 (1991). Therefore, in conclusion, none of the currently utilized protein-based injectable materials appears to be totally satisfactory for the augmentation and/or repair of the subjacent dermis and soft tissue.

The various complications associated with the utilization of the aforementioned materials have prompted experimentation with the implantation (grafting) of viable, living tissue to facilitate augmentation and/or repair of the subjacent dermis and soft tissue. For example, surgical correction of various defects has been accomplished by initial removal and subsequent re-implantation of the excised adipose tissue either by injection (see e.g., Davies et al., Arch. of Otolaryngology-Head and Neck Surgery 121:95 (1995); McKinney & Pandya, Aesthetic Plastic Surgery 18:383 (1994); and Lewis, Aesthetic Plastic Surgery 17:109 (1993)) or by the larger scale surgical-implantation (see e.g., Ersck, Plastic & Reconstructive Surgery 87:219 (1991)). To perform both of the aforementioned techniques a volume of adipose tissue equal or greater than is required for the subsequent augmentation or repair procedure must be removed from the patient. Thus, for large scale repair procedures (e.g., breast reconstruction) the amount of adipose tissue which can be surgically-excised from the patient may be limiting. In addition, other frequently encountered difficulties with the aforementioned methodologies include non-uniformity of the injectate, unpredictable longevity of the aesthetic effects, and a 4-6 week period of post-injection inflammation and swelling. In contrast, in a preferred embodiment, the present invention utilizes the surgical engraftment of autologous adipocytes which have been cultured on a solid support typically derived from, but not limited to, collagen or isolated extracellular matrix. The culture may be established from a simple skin biopsy specimen and the amount of adipose tissue which can be subsequently cultured in vitro is not limited by the amount of adipose tissue initially excised from the patient.

Living skin equivalents have been examined as a methodology for the repair and/or replacement of human skin. Split thickness autographs, epidermal autographs (cultured allogenic keratinocytes), and epidermal allographs (cultured allogenic keratinocytes) have been used with a varying degree of success. However, unfortunately, these forms of treatment have all exhibited numerous disadvantages. For example, split thickness autographs generally show limited tissue expansion, require repeated surgical operations, and give rise to unfavorable aesthetic results. Epidermal autographs require long periods of time to be cultured, have a low success ("take") rate of approximately 30-48%, frequently form spontaneous blisters, exhibit contraction to 60-70% of their original size, are vulnerable during the first 15 days of engraftment, and are of no use in situations where there is both epidermal and dermal tissue involvement. Similarly, epidermal allografts (cultured allogenic keratinocytes) exhibit many of the limitations which are inherent in the use of epidermal autographs. Additional methodologies have been examined which involve the utilization of irradiated cadaver dermis. However, this too has met with limited success due to, for example, graft rejection and unfavorable aesthetic results.

Living skin equivalents comprising a dermal layer of rodent fibroblast cells cast in soluble collagen and an epidermal layer of cultured rodent keratinocytes have been successfully grafted as allografts onto Sprague Dawley rats by Bell et al., J. Investigative Dermatology 81:2 (1983). Histological examination of the engrafted tissue revealed that the epidermal layer had fully differentiated to form desmonosomes, tonofilaments, keratohyalin, and a basement lamella. However, subsequent attempts to reproduce the living skin equivalent using human fibroblasts and keratinocytes has met with only limited success. In general, the keratinocytes failed to fully differentiate to form a basement lamella and the dermoepidermal junction was a straight line.

The present invention includes the following methodologies for the repair and/or augmentation of various skin defects: (1) the injection of autologously cultured dermal or fascial fibroblasts into various layers of the skin or injection directly into a "pocket" created in the region to be repaired or augmented, or (2) the surgical engraftment of "strands" derived from autologous dermal and fascial fibroblasts which are cultured in such a manner as to form a three-dimensional "tissue-like" structure similar to that which is found in vivo. Moreover, the present invention also differs on a two-dimensional level in that "true" autologous culture and preparation of the cells is performed by utilization of the patient's own cells and serum for in vitro culture.

III. Vocal Cord Tissue Augmentation and/or Repair

Phonation is accomplished in humans by the passage of air past a pair of vocal cords located within the larynx. Striated muscle fibers within the larynx, comprising the constrictor muscles, function so as to vary the degree of tension in the vocal cords, thus regulating both their overall rigidity and proximity to one another to produce speech. However, when one (or both) of the vocal cords becomes totally or partially immobile, there is a diminution in the voice quality due to an inability to regulate and maintain the requisite tension and proximity of the damaged cord in relation to that of the operable cord. Vocal cord paralysis may be caused by cancer, surgical or mechanical trauma, or similar afflictions which render the vocal cord incapable of being properly tensioned by the constrictor muscles.

One therapeutic approach which has been examined to allow phonation involves the implantation or injection of biocompatible materials. It has long been recognized that a paralyzed or damaged vocal cord may be repositioned or supported so as to remain in a fixed location relative to the operable cord such that the unilateral vibration of the operable cord produces an acceptable voice pattern. Hence, various surgical methodologies have been developed which involve the formation of an opening in the thyroid cartilage and subsequently providing a means for the support and/or repositioning of the paralyzed vocal cord.

For example, injection of TEFLON® into the paralyzed vocal cord to increase its inherent "bulk" has been described. See e.g., von Leden et al., Phonosurgery 3:175 (1989). However, this procedure is now considered unacceptable due to the inability of the injected TEFLON® to close large glottic gaps, as well as its tendency to induce inflammatory reactions resulting in the formation of fibrous infiltration into the injected cord. See e.g., Maves et al., Phonosurgery: Indications and Pitfalls 98:577. (1989). Moreover, removal of the injected TEFLON® may be quite difficult should it subsequently be desired or become necessary.

Another methodology for supporting the paralyzed vocal cord which has been employed involves the utilization of a custom-fitted block of siliconized rubber (SILASTIC®). In order to ensure the proper fit of the implant, the surgeon hand carves the SILASTIC® block during the procedure in order to maximize the ability of the patient to phonate The patient is kept under local anesthesia so that he or she can produce sounds to test the positioning of the implant. Generally, the implanted blocks are formed into the shape of a wedge which is totally implanted within the thyroid cartilage or a flanged plug which can be moved back-and-forth within the opening in the thyroid cartilage to fine-tune the voice of the patient.

Although SILASTIC® implants have proved to be superior over TEFLON® injections, there are several areas of dissatisfaction with the procedure including difficulty in the carving and insertion of the block, the large amount of time required for the procedure, and a lack of an efficient methodology for locking the block in place within the thyroid cartilage. In addition, vocal cord edema, due to the prolonged nature of the procedure and repeated voice testing during the operation, may also prove problematic in obtaining optimal voice quality.

Other methodologies which have been utilized in the treatment of vocal cord paralysis and damage include GEL-FOAM® hydroxyapatite, and porous ceramic implants, as well as injections of silicone and collagen. See e.g., Koufman, Laryngoplastic Phonosurgery (1988). However, these materials have also proved to be less than ideal due to difficulties in the sizing and shaping of the solid implants as well as the potential for subsequent immunogenic reactions. Therefore, there still remains a need for the development of a methodology which allows the efficacious treatment of vocal cord paralysis and/or damage.

SUMMARY OF THE INVENTION

The present invention discloses a methodology for the long-term augmentation and/or repair of dermal, subcutaneous, or vocal cord tissue by the injection or direct surgical placement/implantation of: (1) autologous cultured fibroblasts derived from connective tissue, dermis, or fascia; (2) lamina propria tissue; (3) fibroblasts derived from the lamina propria; or (4) adipocytes. The fibroblast cultures utilized for the augmentation and/or repair of skin defects are derived from either connective tissue, dermal, and/or fascial fibroblasts. Typical defects of the skin which can be corrected with the injection or direct surgical placement of autologous fibroblasts or adipocytes include rhytids, stretch marks, depressed scars, cutaneous depressions of traumatic or non-traumatic origin, hypoplasia of the .lip, and/or scarring from acne vulgaris. Typical defects of the vocal cord which can be corrected by the injection or direct surgical placement of lamina propria or autologous cultured fibroblasts from lamina propria include scarred, paralyzed, surgically or traumatically injured, or congenitally underdeveloped vocal cord(s).

The use of autologous cultured fibroblasts derived from the dermis, fascia, connective tissue, or lamina propria mitigates the possibility of an immunogenic reaction due to a lack of tissue histocompatibility. This provides vastly superior post-surgical results. In a preferred embodiment of the present invention, fibroblasts of connective tissue, dermal, or facial origin as well as adipocytes are derived from full-thickness biopsies of the skin. Similarly, lamina propria tissue or fibroblasts derived from the lamina propria are obtained from vocal cord biopsies. It should be noted that the aforementioned tissues are derived from the individual who will subsequently undergo the surgical procedure, thus mitigating the potential for an immunogenic reaction. These tissues are then expanded in vitro utilizing standard tissue culture methodologies.

Additionally, the present invention further provides a methodology of rendering the cultured cells substantially free of potentially immunogenic serum-derived proteins by late-stage passage of the cultured fibroblasts, lamina propria tissue, or adipocytes in serum-free medium or in the patient's own serum. In addition, immunogenic proteins may be markedly reduced or eliminated by repeated washing in phosphate-buffered saline (PBS) or similar physiologically-compatible buffers.

DESCRIPTION OF THE INVENTION

I. Histology of the Skin

The skin is composed of two distinct layers: the epidermis, a specialized epithelium derived from the ectoderm, and beneath this, the dermis, of vascular dense connective tissue, a derivative of mesoderm. These two layers are firmly adherent to one another and form a region which varies in overall thickness from approximately 0.5 to 4 mm in different areas of the body. Beneath the dermis is a layer of loose connective tissue which varies from areolar to adipose in character. This is the superficial fascia of gross anatomy, and is sometimes referred to as the hypodermis, but is not considered to be part of the skin. The dermis is connected to the hypodermis by connective tissue fibers which pass from one layer to the other.

A. Epidermis

The epidermis, a stratified squamous epithelium, is composed of cells of two separate and distinct origins. The majority of the epithelium, of ectodermal origin, undergoes a process of keratinization resulting in the formation of the dead superficial layers of skin. The second component comprises the melanocytes which are involved in the synthesis of pigmentation via melanin. The latter cells do not undergo the process of keratinization. The superficial keratanized cells are continuously lost from the surface and must be replaced by cells that arise from the mitotic activity of cells of the basal layers of the epidermis. Cells which result from this proliferation are displaced to higher levels, and as they move upward they elaborate keratin, which eventually replaces the majority of the cytoplasm. As the process of keratinization continues the cell dies and is finally shed. Therefore, it should be appreciated that the structural organization of the epidermis into layers reflects various stages in the dynamic process of cellular proliferation and differentiation.

B. Dermis

It is frequently difficult to quantitatively differentiate the limits of the dermis as it merges into the underlying subcutaneous layer (hypodermis). The average thickness of the dermis varies from 0.5 to 3 mm and is further subdivided into two strata—the papillary layer superficially and the reticular layer beneath. The papillary layer is composed of thin collagenous, reticular, and elastic fibers arranged in an extensive network.

Just beneath the epidermis, reticular fibers of the dermis form a close network into which the basal processes of the cells of the stratum germinativum are anchored. This region is referred to as the basal lamina.

The reticular layer is the main fibrous bed of the dermis. Generally, the papillary layer contains more cells and smaller and finer connective tissue fibers than the reticular layer. It consists of coarse, dense, and interlacing collagenous fibers, in which are intermingled a small number of reticular fibers and a large number of elastic fibers. The predominant arrangement of these fibers is parallel to the surface of the skin. The predominant cellular constituent of the dermis are fibroblasts and macrophages. In addition, adipose cells may be present either singly or, more frequently, in clusters. Owing to the direction of the fibers, lines of skin tension, Langer's lines, are formed. The overall direction of these lines is of surgical importance since incisions made parallel with the lines tend to gape less and heal with less scar tissue formation than incisions made at right-angles or obliquely across the lines. Pigmented, branched connective tissue cells, chromatophores, may also be present. These cells do not elaborate pigment but, instead, apparently obtain it from melanocytes. Smooth muscle fibers may also be found in the dermis. These fibers are arranged in small bundles in connection with hair follicles (arrectores pilorum muscles) and are scattered throughout the dermis in considerable numbers in the skin of the nipple, penis, scrotum, and parts of the perineum. Contraction of the muscle fibers gives the skin of these regions a wrinkled appearance. In the face and neck, fibers of some skeletal muscles terminate in delicate elastic fiber networks of the dermis.

C. Adipose Tissue/Adipocytes

Fat cells; or adipocytes, are scattered in areolar connective tissue. When adipocytes form large aggregates, and are the principle cell type, the tissue is designated adipose tissue. Adipocytes are fully differentiated cells and are thus incapable of undergoing mitotic division. New adipocytes therefore, which may develop at any time within the connective tissue, arise as a result of differentiation of more primitive cells. Although adipocytes, prior to the storage of lipid, resemble fibroblasts, it is likely that they arise directly from undifferentiated mesenchymal tissue.

Each adipocyte is surrounded by a web of fine reticular fibers; in the spaces between are found fibroblasts, lymphoid cells, eosinophils, and some mast cells. The closely spaced adipocytes form lobules, separated by fibrous septa. In addition, there is a rich network of capillaries in and between the lobules. The richness of the blood supply is indicative of the high rate of metabolic activity of adipose tissue.

It should be appreciated that adipose tissue is not static. There is a dynamic balance between lipid deposit and withdrawal. The lipid contained within adipocytes may be derived from three sources. Adipocytes, under the influence of the hormone insulin, can synthesize fat from carbohydrate. They can also produce fat from various fatty acids which are derived from the initial breakdown of dietary fat. Fatty acids may also be synthesized from glucose in the liver and transported to adipocytes as serum lipoproteins. Fats derived from different sources also differ chemically. Dietary fats may be saturated or unsaturated, depending upon the individual diet. Fat which is synthesized from carbohydrate is generally saturated. Withdrawals of fat result from enzymatic hydrolysis of stored fat to release fatty acids into the blood stream. However, if there is a continuous supply of exogenous glucose, then fat hydrolysis is negligible. The normal homeostatic balance is affected by hormones, principally insulin, and by the autonomic nervous system, which is responsible for the mobilization of fat from adipose tissue.

Adipose tissue may develop almost anywhere areolar tissue is prevalent, but in humans the most common sites of adipose tissue accumulation are the subcutaneous tissues (where it is referred to as the panniculus adiposus), in the mesenteries and omenta, in the bone marrow, and surrounding the kidneys. In addition to its primary function of storage and metabolism of neutral fat, in the subcutaneous tissue, adipose tissue also acts as a shock absorber and insulator to prevent excessive heat loss or gain through the skin.

II. Histology of the Larynx and Vocal Cords

The larynx is that part of the respiratory system which connects the pharynx and trachea. In addition to its function as part of the respiratory system, it plays an important role in phonation (speech). The wall of the larynx is composed of a "skeleton" of hyaline and elastic cartilages, collagenous connective tissue, striated muscle, and mucous glands. The major cartilages of the larynx (the thyroid, cricoid, and arytenoids) are hyaline, whereas the smaller cartilages (the corniculates, cuneifomms, and the tips of the arytenoids) are elastic, as is the cartilage of the epiglottis. The aforementioned cartilages, together with the hyoid bone, are connected by three large, flat membranes: the thyrohyoid, the quadrates, and the cricovocal. These are composed of dense fibroconnective tissue in which many elastic fibers are present, particularly in the cricovocal membrane. The true and false vocal cords (vocal- and vestibular ligaments) are, respectively, the free upper boarders of the cricovocal (cricothyroid) and the free lower boarders of the quadrate (aryepiglottic) membranes. Extending laterally on each side between the true and false cords are the sinus and saccule of the larynx, a small slit-like diverticulum. Behind the cricoid and arytenoid cartilages, the posterior wall of the pharynx is formed by the striated muscle of the pharyngeal constrictor muscles.

The epithelium of the mucous membrane of the larynx varies with location. For example, over the vocal folds, the lamina propria of the stratified squamous epithelium is extremely dense and firmly bound to the underlying connective tissue of the vocal ligament. While there is no true submucosa in the larynx, the lamina propria of the mucous membrane is thick and contains large numbers of elastic fibers.

III. Methodologies

A. In Vitro Cell Culture of Fibroblasts or Lamina Propria

While the present invention may be practiced by utilizing any type of non-differentiated mesenchymal cell found in the skin which can be expanded in in vitro culture, fibroblasts derived from dermal, connective tissue, fascial, lamina proprial tissues, adipocytes, and/or extracellular tissues derived from the cells are utilized in a preferred embodiment due to their relative ease of insulation and in vitro expansion in tissue culture. In general, tissue culture techniques which are suitable for the propagation of non-differnentiated mesenchymal cells may be used to expand the aforementioned cells/tissue and practice the present invention as further discussed below. See e.g., Culture of Animal Cells: A Manual of Basic Techniques, Freshney, R. I. eds., (Alan R. Liss & Co., New York 1987); Animal Cell Culture: A Practical Approach, Freshney, R. I. ed., (IRL Press, Oxford, England 1986), whose references are incorporated herein by reference.

The utilization of autologous engraftment is a preferred therapeutic methodology due to the potential for graft rejection associated with the use of allograft-based engraftment. Autologous grafts (i.e., those derived directly from the patient) ensure histocompatibility by initially obtaining a tissue sample via biopsy directly from the patient who will be undergoing the corrective surgical procedure and then subsequently culturing fibroblasts derived from the dermal, connective tissue, fascial, or lamina proprial regions contained therein.

While the following sections will primarily discuss the autologous culture of fibroblasts of connective tissue, dermal, or fascial origins, in vitro culture of lamina propria tissue may also be established utilizing analogous methodologies. An autologous fibroblast culture is preferably initiated by the following methodology. A full-thickness biopsy of the skin (~3×6 mm) is initially obtained through, for example, a punch biopsy procedure. The specimen is repeatedly washed with antibiotic and anti-fungal agents prior to culture. Through a process of sterile microscopic dissection, the keratinized tissue-containing epidermis and subcutaneous adipocyte-containing tissue is removed, thus ensuring that the resultant culture is substantially free of non-fibroblast cells (e.g., adipocytes and keratinocytes). The isolated adipocytes-containing tissue may then be utilized to establish adipocyte cultures. Alternately, whole tissue may be cultured and fibroblast-specific growth medium may be utilized to "select" for these cells.

Two methodologies are generally utilized for the autologous culture of fibroblasts in the practice of the present invention mechanical and enzymatic. In the mechanical methodology, the fascia, dermis, or connective tissue is initially dissected out and finely divided with scalpel or scissors. The finely minced pieces of the tissue are initially placed in 1-2 ml of medium in either a 5 mm petri dish (Costar), a 24 multi-well culture plate (Corning), or other appropriate tissue culture vessel. Incubation is preferably performed at 37° C. in a 5% $CO_2$ atmosphere and the cells are incubated until a confluent monolayer of fibroblasts has been obtained. This may require up to 3 weeks of incubation. Following the establishment of confluence, the monolayer is trypsinized to release the adherent fibroblasts from the walls of the culture vessel. The suspended cells are collected by centrifugation, washed in phosphate-buffered saline, and resuspended in culture medium and placed into larger culture vessels containing the appropriate complete growth medium.

In a preferred embodiment of the enzymatic culture methodology, pieces of the finely minced tissue are digested with a protease for varying periods of time. The enzymatic concentration and incubation time are variable depending upon the individual tissue source, and the initial isolation of the fibroblasts from the tissue as well as the degree of subsequent outgrowth of the cultured cells are highly dependent upon these two factors. Effective proteases include, but are not limited to, trypsin, chymotrypsin, papain, chymopapain, and similar proteolytic enzymes. Preferably, the tissue is incubated with 200-1000 U/ml of collagenase type II for a time period ranging from 30 minutes to 24 hours, as collagenase type II was found to be highly efficacious in providing a high yield of viable fibroblasts. Following enzymatic digestion, the cells are collected by centrifugation and resuspended into fresh medium in culture flasks.

Various media may be used for the initial establishment of an in vitro culture of human fibroblasts. Dulbecco's Modified Eagle Medium (DMEM, Gibco/BRL Laboratories) with concentrations of fetal bovine serum (FBS), cosmic calf serum (CCS), or the patient's own serum varying from 5-20% (v/v)—with higher concentrations resulting in faster culture growth—are readily utilized for fibroblast culture. It should be noted that substantial reductions in the concentration of serum (i.e., 0.5% v/v) results in a loss of cell viability in culture. In addition, the complete culture medium typically contains L-glutamine, sodium bicarbonate, pyridoxine hydrochloride, 1 g/liter glucose, and gentamycin sulfate. The use of the patient's own serum mitigates the possibility of subsequent immunogenic reaction due to the presence of constituent antigenic proteins in the other serums.

Establishment of a fibroblast cell line from an initial human biopsy specimen generally requires 2 to 3.5 weeks in total. Once the initial culture has reached confluence, the cells may be passaged into new culture flasks following trypsinization by standard methodologies known within the relevant field. Preferably, for expansion, cultures are "split" 1:3 or 1:4 into T-150 culture flasks (Corning) yielding ~$5 \times 10^7$ cells/culture vessel. The capacity of the T-150 culture flask is typically reached following 5-8 days of culture at which time the cultured cells are found to be confluent.

Cells are preferably removed for freezing and long-term storage during the early passage stages of culture, rather than the later stages due to the fact that human fibroblasts are capable of undergoing a finite numbers of passages. Culture medium containing 70% DMEM growth medium, 10% (v/v) serum, and 20% (v/v) tissue culture grade dimethylsulfoxide (DMSO, Gibco/BRL) may be effectively utilized for freezing of fibroblast cultures. Frozen cells can subsequently be used to inoculate secondary cultures to obtain additional fibroblasts for use in the original patient, thus doing way with the requirement to obtain a second biopsy specimen.

To minimize the possibility of subsequent immunogenic reactions in the engraftment patient, the removal of the various antigenic constituent proteins contained within the serum may be facilitated by collection of the fibroblasts by centrifugation, washing the cells repeatedly in phosphate-buffered saline (PBS), and then either re-suspending or culturing the washed fibroblasts for a period of 2-24 hours in serum-free medium containing requisite growth factors which are well known in the field. Culture media include, but are not limited to, Fibroblast Basal Medium (FBM). Alternately, the fibroblasts may be cultured utilizing the patient's own serum in the appropriate growth medium.

After the culture has reached a state of confluence, the fibroblasts may either be processed for injection or further cultured to facilitate the formation of a three-dimensional "tissue" for subsequent surgical engraftment. Fibroblasts utilized for injection consist of cells suspended in a collagen gel matrix. The collagen gel matrix is preferably comprised of a mixture of 2 ml of a collagen solution containing 0.5 to 1.5 mg/ml collagen in 0.05% acetic acid, 1 ml of DMEM medium, 270 µl of 7.5% sodium bicarbonate, 48 µl of 100 µg/ml solution of gentamycin sulfate, and up to $5 \times 10^6$ fibroblast cells/ml of collagen gel. Following the suspension of the fibroblasts in the collagen gel matrix, the suspension is allowed to solidify for approximately 15 minutes at room temperature or 37° C. in a 5% $CO_2$ atmosphere. The collagen may be derived from human or bovine sources, or from the patient and may be enzymatically- or chemically-modified (e.g., atelocollagen).

Three-dimensional "tissue" is formed by initially suspending the fibroblasts in the collagen gel matrix as described above. Preferably, in the culture of three-dimensional tissue, full-length collagen is utilized, rather than truncated or modified collagen derivatives. The resulting suspension is then placed into a proprietary "transwell" culture system which is typically comprised of culture well in which the lower growth medium is separated from the upper region of the culture well by a microporous membrane. The microporous membrane typically possesses a pore size ranging from 0.4 to 8 µm in diameter and is constructed from materials including, but not limited to, polyester, nylon, nitrocellulose, cellulose acetate, polyacrylamide, cross-linked dextrose, agarose, or other similar materials. The culture well component of the transwell culture system may be fabricated in any desired shape or size (e.g., square, round, ellipsoidal, etc.) to facilitate subsequent surgical tissue engraftment and typically holds a volume of culture medium ranging from 200 µl to 5 ml. In general, a concentration ranging from $0.5 \times 10^6$ to $10 \times 10^6$ cells/ml, and preferably $5 \times 10^6$ cells/ml, are inoculated into the collagen/fibroblast-containing suspension as described above. Utilizing a preferred concentration of cells (i.e., $5 \times 10^6$ cells/ml), a total of approximately 4-5 weeks is required for the formation of a three-dimensional tissue matrix. However, this time may vary with increasing or decreasing concentrations of inoculated cells. Accordingly, the higher the concentration of cells utilized the less time due to a higher overall rate of cell proliferation and replacement of the exogenous collagen with endogenous collagen and other constituent materials which form the extracellular matrix synthesized by the cultured fibroblasts. Constituent materials which form the extracellular matrix include, but are not limited to, collagen, elastin, fibrin, fibrinogen, proteases, fibronectin, laminin, fibrellins, and other similar proteins. It should be noted that the potential for immunogenic reaction in the engrafted patient is markedly reduced due to the fact that the exogenous collagen used in establishing the initial collagen/fibroblast-containing suspension is gradually replaced during subsequent culture by endogenous collagen and extracellular matrix materials synthesized by the fibroblasts.

B. In Vitro Culture of Adipocytes

Adipocytes require a "feeder-layer" or other type of solid support on which to grow. One potential solid support may be provided by utilization of the previously discussed collagen gel matrix. Alternately, the solid support may be provided by cultured extracellular matrix. In general, the in vitro culture of adipocytes is performed by the mechanical or enzymatic disaggregation of the adipocytes from adipose tissue derived from a biopsy specimen. The adipocytes are "seeded" onto the surface of the aforementioned solid support and allowed to grow, until near-confluence is reached. The adipocytes are removed by gentle scraping of the solid surface. The isolated adipocytes are then cultured in the same manner as utilized for fibroblasts as previously discussed in Section III A.

C. Isolation of the Extracellular Matrix

The extracellular matrix (ECM) may be isolated in either a cellular or acellular form. Constituent materials which form the ECM include, but are not limited to, collagen, elastin, fibrin, fibrinogen, proteases, fibronectin, laminin, fibrellins, and other similar proteins. ECM is typically isolated by the initial culture of cells derived from skin or vocal cord biopsy specimens as previously described. After the cultured cells have reached a minimum of 25-50% sub-confluence, the ECM may be obtained by mechanical, enzymatic, chemical, or denaturant treatment. Mechanical collection is performed by scraping the ECM off of the plastic culture vessel and re-suspending in phosphate-buffered saline (PBS). If desired, the constituent cells are lysed or ruptured by incubation in hypotonic saline containing 5 mM EDTA. Preferably, however, scraping followed by PBS re-suspension is generally utilized. Enzymatic treatment involves brief incubation with a proteolytic enzyme such as trypsin. Additionally, the use of detergents such as sodium dodesyl sulfate (SDS) or treatment with denaturants such as urea or dithiotheritol (DTT) followed by dialysis against PBS, will also facilitate the release of the ECM from surrounding associated tissue.

The isolated ECM may then be utilized as a "filler" material in the various augmentation or repair procedures disclosed in the present application. In addition, the ECM may possess certain cell growth- or metabolism-promoting characteristics.

D. In Vitro Culture of Fetal or Juvenile Cells or Tissues

In another preferred embodiment, rather than utilizing the patient's own tissue, all of the aforementioned cells, cell suspensions, or tissues may be derived from fetal or juvenile sources. Fetal cells lack the immunogenic determinants responsible for eliciting the host graft-rejection reaction and thus may be utilized for engraftment procedures with little or no probability of a subsequent immunogenic reaction. An acellular ECM may also be obtained from fetal ECM by hypotonic lysing of juvenile sources may be used as a "filler" material in the various augmentation or repair procedures disclosed in the present application. In addition, the fetal or juvenile ECM may possess certain cell growth- or metabolism-promoting characteristics.

E. Injection of Autologous Cultured Dermal/Fascial Fibroblasts

To augment or repair dermal detects, autologously cultured fibroblasts are injected initially into the lower dermis, next in the upper and middle dermis, and finally in the subcutaneous regions of the skin as to form raised areas or "wheals." The fibroblast suspension is injected via a syringe with a needle ranging frog 30 to 18 gauge, with the gauge of the needle being dependent upon such factors as the overall viscosity of the fibroblast suspension and the type of anesthetic utilized. Preferably, needles ranging from 22 to 18 gauge and 30 to 27 gauge are used with general and local anesthesia, respectively.

To inject the fibroblast suspension into the lower dermis, the needle is placed at approximately a 45° angle to the skin with the bevel of the needle directed downward. To place the fibroblast suspension into the middle dermis the needle is placed at approximately a 20-30° angle. To place the suspension into the upper dermis, the needle is placed almost horizontally (i.e., ~10-15° angle). Subcutaneous injection is accomplished by initial placement of the needle into the subcutaneous tissue and injection of the fibroblast suspension during subsequent needle withdrawal. In addition, it should be noted that the needle is preferably inserted into the skin from various directions such that the needle tract will be somewhat different with each subsequent injection. This technique facilitates a greater amount of total skin area receiving the injected fibroblast suspension.

Following the aforementioned injections, the skin should be expanded and possess a relatively taut feel. Care should be taken so as not to produce an overly hard feel to the injected region. Preferably, depressions or rhytids appear elevated following injection and should be "overcorrected" by a slight degree of over-injection of the fibroblast suspension, as typically some degree of settling or shrinkage will occur postoperatively.

In some scenarios, the injections may pass into deeper tissue layers. For example, in the case of lip augmentation or repair, a preferred manner of injection is accomplished by initially injecting the fibroblast suspension into the dermal and subcutaneous layers as previously described, into the skin above the lips at the vermillion border. In addition, the vertical philtrum may also be injected. The suspension is subsequently injected into the deeper tissues of the lip, including the muscle, in the manner described for subcutaneous injection.

F. Surgical Placement of Autologously Cultured Dermal/Fascial Fibroblast Strands In a preferred methodology utilized to augment or repair the skin and/or lips by the surgical placement of autologously cultured dermal and/or fascial fibroblast strands, a needle (the "passer needle") is selected which is larger in diameter and greater in length than the area to be repaired or augmented. The passer needle is then placed into the skin and threaded down the length of the area. Guide sutures are placed at both ends through the dermal or fascial fibroblast strand. One end of the guide suture is fixed to a Keith needle which is subsequently placed through the passer needle. The guide suture is brought out through the skin on the side furthest (distal point) from the initial entry point of the passer needle. The dermal or fascial fibroblast graft is then pulled into the passer needle and its position may be adjusted by pulling on the distal point guide suture or, alternately, the guide suture closest to the passer needle entry point. While the dermal or fascial strand is held in place by the distal point suture, the passer needle is pulled backward and removed, thus resulting in the final placement of the graft following the final cutting of the remaining suture.

Generally, the fascial or dermal graft is placed into the subcutaneous layer of the skin. However, in some situations, it may be placed either more deeply or superficially.

If the area to be repaired or augmented is either smaller or larger than would be practical to fill with the aforementioned needle method, a subcutaneous "pocket" may be created with a myringotomy knife, scissors, or other similar instrument. A piece of dermis or fascia is then threaded into this area by use of guide sutures and passer needle, as described above.

G. Injection of Cells or Other Substances into the Vocal Cords or Larynx

Generally, it is not possible to inject cellular matter or other substances directly into the vocal cord epithelium due to its extreme thinness. Accordingly, injections are usually made into the lamina propria layer or the muscle itself. Generally, lamina propria tissue (finely minced if required for injection), fibroblasts derived from lamina propria tissue, or gelatinous substances are utilized for injection. The preferable methodology consists of injection directly into the space containing the lamina propria, specifically into Reinke's space. Injection is accomplished by use of laryngeal injection needles of the smallest possible gauge which will accommodate the injectate without the use of extraneous pressure during the actual injection process. This is a subjective process as to the overall "feel" and the use of too much pressure may irreparably damage the injected cells. The material is injected via a syringe with a needle ranging from 30 to 18 gauge, with the gauge of the needle being dependent upon such factors as the overall viscosity of the injectate and the type of anesthetic utilized. Preferably, needles ranging from 22 to 18 gauge and 30 to 27 gauge are used with general and local anesthesia, respectively. If required, several injections may be performed along the length of the vocal cord.

To medialize a vocal cord with autologously cultured fascial or dermal fibroblasts, the materials are preferably injected directly into the tissue lateral or at the lateral edge of the vocal cord. The fibroblasts may be injected into scar, Reinke's space, or muscle, depending upon the specific vocal cord pathology. Preferably, it would be injected into the muscle.

The procedure may be performed under general, local, topical, monitored, or with no anesthesia, depending upon patient compliance and tolerance, the amount of injected material, and the type of injection performed.

If a greater degree of augmentation is required, a "pocket" may be created by needle dissection. Alternately, laryngeal microdisection, using knives and dissectors, may be performed. The desired material is then placed into the pocket with laryngeal forceps, or directly injected, depending upon the size of the pocket, the size of the graft material, the anesthesia, and the open access. If the pocket is left open after the procedure, it is preferably closed with sutures, adhesive, or a laser, depending upon the size and availability of these materials and the individual preferences of the surgeon.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein.

What is claimed:

1. A method of treating a tissue associated with a defect in a patient using autologous materials derived from the patient, the method comprising: introducing a plurality of autologous adipose cells to the tissue at, or proximal to, the defect of the patient after the plurality of autologous adipose cells have been cultured in vitro to expand the number of adipocyte cells in at least one medium that comprises autologous serum.

2. The method of claim 1 wherein extracellular matrix produced in vitro by the autologous adipose cells is introduced into the patient in association with the plurality of autologous adipose cells.

3. The method of claim 1 wherein the adipose cells comprise pre-adipocytes.

4. The method of claim 1 wherein the adipose cells comprise adipocytes.

5. The method of claim 1 wherein the adipose cells comprise nondifferentiated mesenchymal cells.

6. The method of claim 1 wherein fibronectin is introduced into the patient in association with the plurality of autologous adipose cells.

7. The method of claim 1 wherein collagen or modified collagen is introduced into the patient in association with the plurality of autologous adipose cells.

8. The method of claim 1 wherein hyaluronic acid is introduced into the patient in association with the plurality of autologous adipose cells.

9. The method of claim 1 wherein the introduction of the adipose cells into the patient comprises a method chosen from injection, engraftment, engraftment by threading, and direct placement.

10. The method of claim 1 wherein the tissue comprises a member of the group consisting of lower dermis, middle dermis, upper dermis, and skin subcutaneous region.

11. The method of claim 1 wherein the tissue comprises muscle tissue.

12. The method of claim 1 wherein the patient is human.

13. The method of claim 1, wherein the tissue is associated with a defect chosen from the group consisting of wrinkles, rhytids, depressed scar, cutaneous depressions, stretch marks, hyperplasia of the lip, nasolabial fold, melolabial fold, scarring from acne vulgaris, dermal, subcutaneous, skin defect, and post-rhinoplasty irregularity.

14. The method of claim 1 wherein the in vitro cultured cells are introduced into the patient in a mixture with a filler material, wherein the filler material, prior to mixing with the cells, comprises a member of the group consisting of collagen, fibronectin, fibrillin, laminin, elastin, glycosaminoglycan, exogenous extracellular matrix, whole extracellular matrix, and autologous extracellular matrix.

15. A method of treating a tissue associated with a defect in a patient, the method comprising: introducing a plurality of isolated adipose cells to treat the defect of the patient after the plurality of adipose cells have been isolated in vitro.

16. The method of claim 15 wherein the tissue is associated with a defect chosen from the group consisting of wrinkles, rhytids, depressed scar, cutaneous depressions, stretch marks, hyperplasia of the lip, nasolabial fold, melolabial fold, scarring from acne vulgaris, dermal, subcutaneous, skin defect, and post-rhinoplasty irregularity.

17. The method of claim 15 wherein the cultured adipose cells are expanded in vitro.

18. The method of claim 15 wherein the cells are introduced into the patient in a mixture with a filler material, wherein the filler material, prior to mixing with the cells, comprises a member of the group consisting of collagen, fibronectin, fibrillin, laminin, elastin, glycosaminoglycan, exogenous extracellular matrix, whole extracellular matrix, and autologous extracellular matrix.

19. The method of claim 15 wherein the adipose cells comprise adipocytes.

20. The method of claim 15 wherein the adipose cells comprise pre- adipocytes.

21. The method of claim 15 wherein the adipose cells comprise undifferentiated mesenchymal cells.

22. The method of claim 15 wherein the adipose cells have been cultured in vitro to expand the number of adipocyte cells in at least one medium that comprises autologous serum.

23. The method of claim 15 wherein the adipose cells are allogeneic.

24. The method of claim 15 wherein the patient is human.

25. The method of claim 15 wherein the cells are autologous.

26. The method of claim 15 wherein the cells are placed at, or proximal to, the defect.

27. The method of claim 15 wherein the cells are in a suspension.

* * * * *